(12) United States Patent
Huston et al.

(10) Patent No.: US 6,909,495 B2
(45) Date of Patent: Jun. 21, 2005

(54) EMISSIVITY PROBE

(75) Inventors: John T. Huston, Sugar Grove, OH (US); Simon F. Youssef, Lancaster, OH (US)

(73) Assignee: Diamond Power International, Inc., Lancaster, OH (US)

( * ) Notice: Subject to any disclaimer, the term of this patent is extended or adjusted under 35 U.S.C. 154(b) by 337 days.

(21) Appl. No.: 10/218,067

(22) Filed: Aug. 13, 2002

(65) Prior Publication Data
US 2004/0032583 A1 Feb. 19, 2004

(51) Int. Cl.[7] .................................................. G01J 5/48
(52) U.S. Cl. ........................................ 356/43; 110/185
(58) Field of Search .......................... 356/43, 432–435, 356/445–448; 348/83, 164; 110/185–190, 195, 233–234, 341–345, 349

(56) References Cited

U.S. PATENT DOCUMENTS

| | | |
|---|---|---|
| 3,021,386 A | 2/1962 | Clark |
| 4,539,588 A | 9/1985 | Ariessohn et al. |
| 4,580,908 A | 4/1986 | Stewen |
| 4,661,694 A | 4/1987 | Corcoran |
| 4,695,878 A | 9/1987 | Levine et al. |
| 4,840,474 A | 6/1989 | Heft et al. |
| 4,870,496 A | 9/1989 | Fantone |
| 4,981,088 A | 1/1991 | Burris |
| 5,010,827 A | 4/1991 | Kychakoff et al. |
| 5,051,821 A | 9/1991 | Vittot et al. |
| RE33,857 E | 3/1992 | Ariessohn et al. |
| 5,094,695 A | 3/1992 | Bailey et al. |
| 5,110,365 A | 5/1992 | Carter |
| 5,139,412 A | 8/1992 | Kychakoff et al. |
| 5,155,358 A | 10/1992 | Larson |
| 5,219,226 A | 6/1993 | James |
| 5,309,230 A | 5/1994 | Blondel et al. |
| 5,355,845 A | 10/1994 | Burgess et al. |
| 5,368,471 A | 11/1994 | Kychakoff et al. |
| 5,462,358 A | 10/1995 | Werner |
| 5,578,995 A | 11/1996 | Bryant et al. |
| 5,592,151 A | 1/1997 | Rolih |
| 5,661,817 A | 8/1997 | Hatlestad et al. |
| 5,665,963 A | 9/1997 | Campbell |
| 5,801,763 A | 9/1998 | Suzuki |
| 5,831,668 A * | 11/1998 | Hirvonen et al. .............. 348/83 |
| 5,910,816 A | 6/1999 | Fontenot et al. |
| 6,069,652 A | 5/2000 | Eversole et al. |
| 6,122,041 A * | 9/2000 | Najm et al. .................... 356/43 |
| 6,150,652 A | 11/2000 | Forsyth |
| 6,239,831 B1 | 5/2001 | Eversole et al. |
| 6,255,650 B1 | 7/2001 | Warner et al. |
| 2002/0003583 A1 | 1/2002 | Arai |
| 2002/0043623 A1 | 4/2002 | Galloway |
| 2002/0044212 A1 | 4/2002 | Hashimoto |

FOREIGN PATENT DOCUMENTS

FR 2 564 970 11/1985

OTHER PUBLICATIONS

Published PCT WO 01/44747 A2, International Publication Date Jun. 21, 2001.
Published PCT WO 01/44747 A3, International Publication Date Jun. 21, 2001.

* cited by examiner

Primary Examiner—Richard A. Rosenberger
Assistant Examiner—Vincent P. Barth
(74) Attorney, Agent, or Firm—Brinks Hofer Gilson & Lione

(57) ABSTRACT

An emissivity probe for measuring reflected energy from interior wall surfaces of large scale boilers. The emissivity probe uses a pair of light guides which respectively receive light energy from the interior of the boiler and that reflected off a wall surface. Using appropriate photo detectors sensitive to a desired light wavelength range, a ratio of the reflected and incident radiation is provided. This provides a measure of the reflectivity of the wall surface. The reflectivity values are used to control boiler cleaning systems.

42 Claims, 8 Drawing Sheets

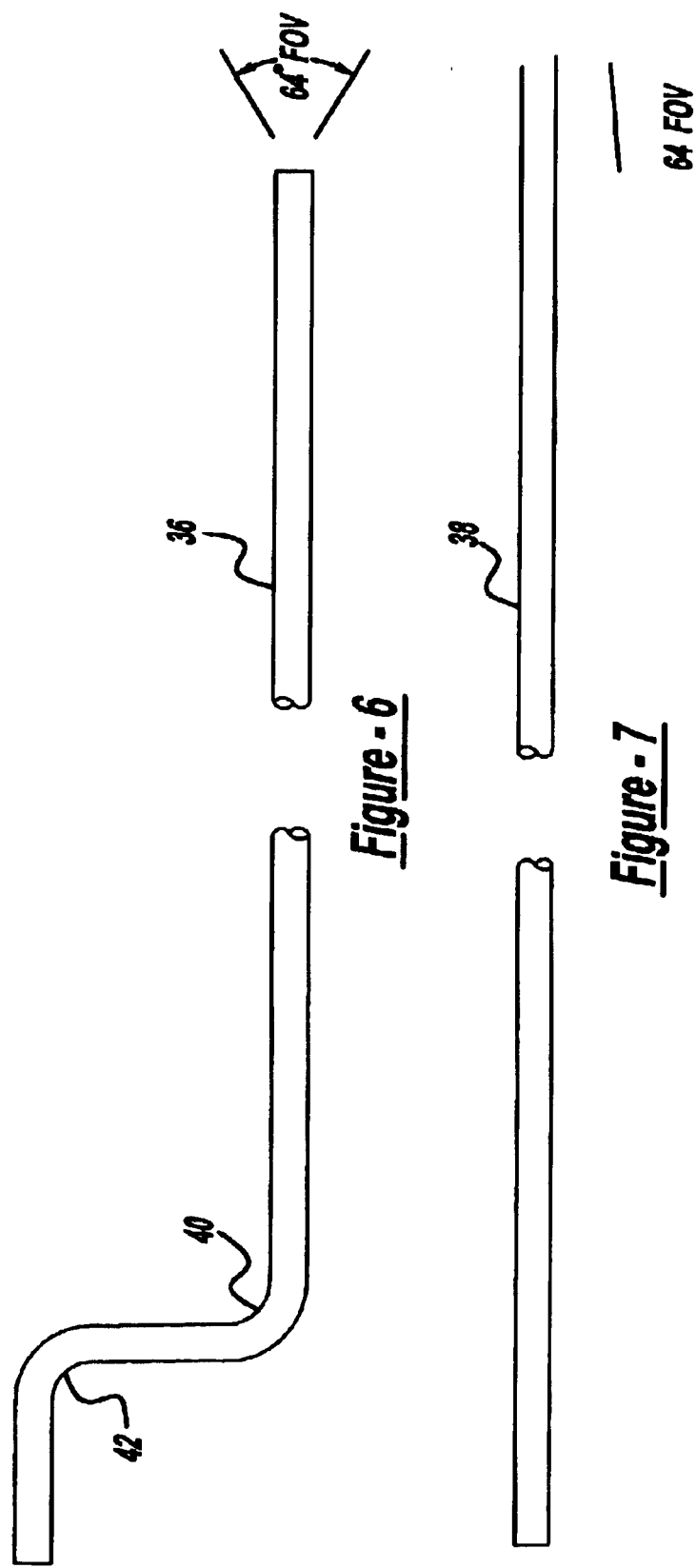

EMISSIVITY PROBE

FIELD OF THE INVENTION

This invention relates to an emissivity probe of a type adapted for evaluating, through optical inputs, the condition of internal surfaces of large scale combustion devices such as utility and processing boilers.

BACKGROUND OF THE INVENTION

In the operation of large scale combustion devices such as coal burning boilers, there is a continual build up of slag deposits on their internal walls and heat transfer surfaces. As the slag builds up on these surfaces, the slag layer reflects some of the radiant heat energy produced within the boiler by combustion and thus, less steam and thermal output is produced by the boiler. Accordingly, it is important to periodically remove the slag layers to maintain efficient operation.

Various means for detecting the presence of slag development on internal surfaces of combustion devices have been developed. One approach is through the monitoring of various operating parameters of the boiler which provide an indirect indication of the development of such slag as efficiency is adversely affected. When slag deposits reach a point where cleaning is needed, various cleaning technologies are used. For example, sootblower systems are used which project a stream of fluid cleaning medium against the surfaces, such as air, steam, or water. These fluids remove the slag through a combination of heat quenching which embrittles the coating and mechanical impact energy which causes the encrustations to lose their adherence to the surfaces and fall away. Other approaches include mechanical rodding and shakers which vibrate the surfaces to remove the layers.

For efficient boiler operation, it is desirable to clean surfaces only when needed. Operating sootblowers causes an efficiency penalty for the boiler when it is not used then at a time when it is actually needed. Operating cleaning systems based strictly on time or other indirect measures can result in operating the cleaning devices on a schedule which is not optimal.

It is known that the inside surfaces of a boiler can be imaged using cameras sensitive to infrared light. These devices employ an objective lens positioned inside the boiler which images a wall surface of the boiler. Although these systems are effective in many applications, they have the shortcomings of high cost and sophistication, as well as the requirement for complex image processing. Moreover, since the wall being imaged is typically some distance from the objective lens, disturbances such as the fireball or products of combustion in the boiler can interfere with the clear visibility of the surfaces being imaged. Such cameras generally have lens tubes of a diameter of two inches or more, which pose installation difficulties in penetrating the boiler outer wall.

Another approach toward detecting the state of cleanliness of interior boiler surfaces is through the use of so-called heat flux sensors. These devices are typically thermocouple elements mounted to the steam tubes which carry the steam being produced by the boiler. When the temperature of the internal surface of the boiler and the steam carried within the pipe adjacent to that surface approach one another, it is then known that the rate of heat transfer from the combustion processes in the boiler has been reduced. This is an indirect indication of the development of slag encrustations and can be used to activate cleaning systems.

There is a need in the art to provide additional mechanisms for the detection of slag build ups on internal surfaces of combustion systems including coal fired boilers. Ideally, the device would be relatively inexpensive to manufacture, install, and use, be durable, require little maintenance, and reliably and accurately detect the presence of slag development.

SUMMARY OF THE INVENTION

In accordance with this invention, an emissivity probe for boiler wall monitoring is provided. The device uses a pair of optical guides, with one optical guide facing and receiving infrared radiation from the internal fireball within the boiler interior. The other optical guide is directed to receive radiation reflected from the wall surface. Photo detectors receive light transmitted by the optical guides, and produce an electrical signal output. By comparing the ratio or difference of these outputs, a measure of the degree to which the surface reflects radiation can be developed. Preferably, the probe is sensitive to radiation in the infrared region of the spectrum and over a band of radiation in the wavelength region of 0.4 to 4.0 microns. Peak sensitivity at around 1.45 microns is particularly suitable as this corresponds with the peak radiation from a source at about 3000° F. Slag encrustations which cause high reflectivity of the surfaces adversely affect heat transfer through the wall and thus such encrustations must be periodically removed. The emissivity probe in accordance with this invention provides a pair of single channel outputs from photodiodes which signals may be easily processed to provide control inputs for the boiler cleaning systems. The probe is further robust and durable in its construction. Due to the small diameter of the tube assembly, the emissivity probe of this invention can be easily installed through the outer wall of a boiler.

Additional benefits and advantages of the present invention will become apparent to those skilled in the art to which the present invention relates from the subsequent description of the preferred embodiment and the appended claims, taken in conjunction with the accompanying drawings.

BRIEF DESCRIPTION OF THE DRAWINGS

FIG. 6 is a side elevational view of the incident optical guide used in the emissivity probe as shown in FIG. 1;

FIG. 7 is a elevational view of a reflective optical guide used in the emissivity probe of FIG. 1;

DETAILED DESCRIPTION OF THE INVENTION

In order to provide more background for a description of the components and features of the emissivity probe of this invention, certain background principles are described. It is generally recognized that heat transfer occurs by three mechanisms; namely, radiation, convection, and conduction. In a coal burning furnace or boiler, heat transfer to the steam pipes primarily occurs through the mechanism of radiation. A well-known equation which describes the transfer of heat through radiation to a surface (wall) is as follows:

$$Q=\sigma \epsilon A(T_f^4-T_w^4)$$

where
A=wall area
$\sigma$=Stefan-Boltzman constant
$\epsilon$=wall emissivity
$T_f$=flame temperature
$T_w$=wall temperature Therefore, a critical component in the transfer of heat to boiler walls is trough its characteristic emissivity ($\epsilon$) factor. Emissivity can also be thought of as the absorbance of radiation by the wall surface. Of the total radiation incident on the wall surface, three related quantities of radiant heat energy can be identified that are related to the wall's characteristics. This relationship can be expressed as follows:

$$\epsilon + \rho + T = 1.0$$

where
$\rho$=reflectance
$T$=transmissance

For boiler tube walls T=0 (i.e. it is opaque to incident radiation) and therefore:

$$\epsilon + \rho = 1.0$$

Therefore by quantifying reflectance ($\rho$), emissivity ($\epsilon$) can be indirectly measured.

The emissivity probe in accordance with this invention utilizes this concept.

And since $\epsilon + \rho = 1.0$, and $$\rho=(Q_{wall}/Q_{incident})$$

$$\epsilon=1.0-(Q_{wall}/Q_{incident})$$

where
$Q_{wall}$=Reflected radiation from the wall
$Q_{incident}$=Incident radiation from the flame Thus by measuring the reflected radiation from the boiler wall ($Q_{wall}$) and the incident radiation from the flame ($Q_{incident}$) a measure of emissivity and therefore absorbance can be made.

As stated previously in this description, the heat transfer characteristics of a coal-fired boiler wall change over time due to the buildup of layers of fouling material on those surfaces which adversely affect absorbance and therefore heat transfer.

Figure 1:
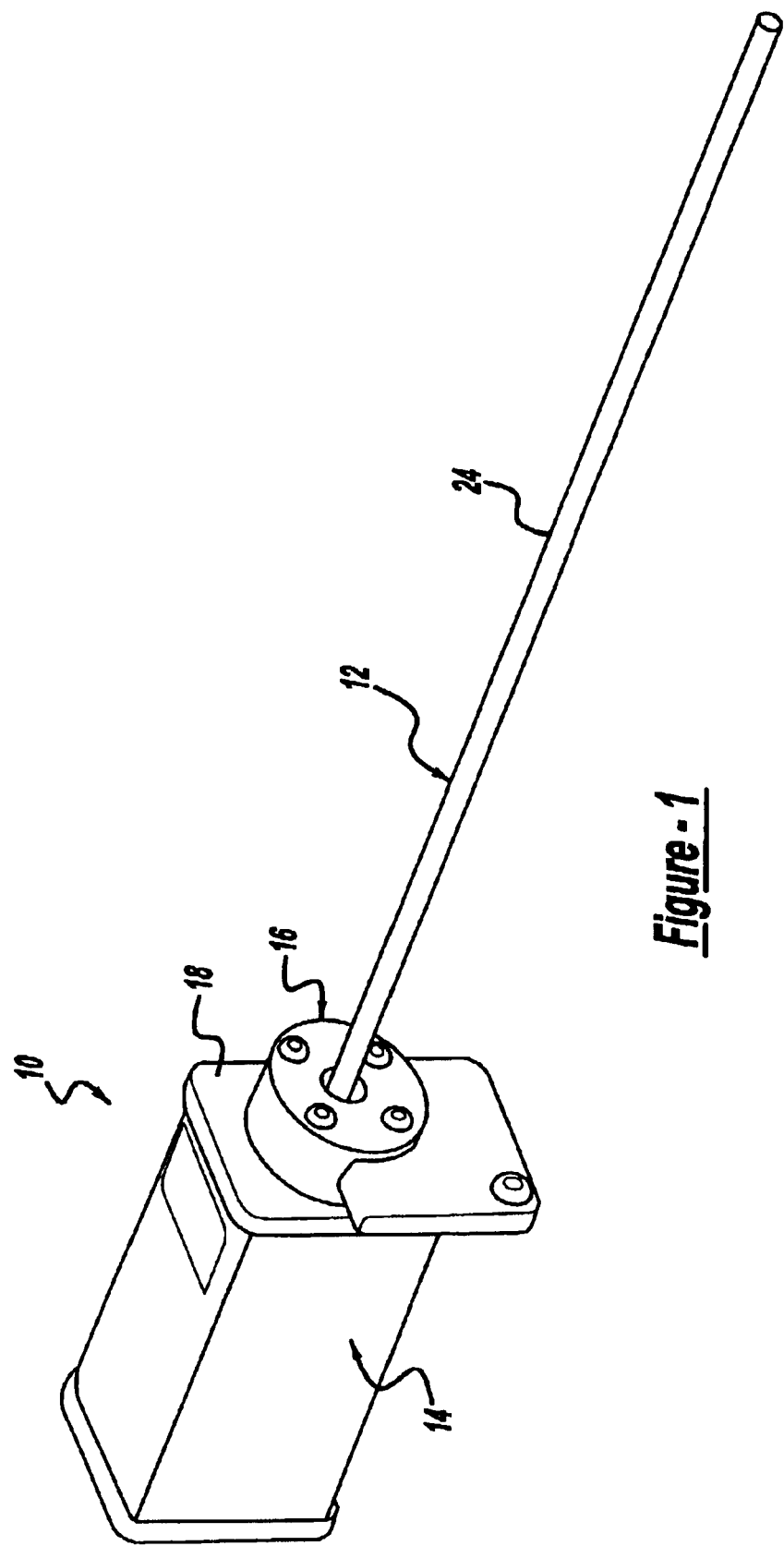
FIG. 1 is a pictorial view of an emissivity probe in accordance with this invention.

FIG. 1 illustrates an emissivity probe in accordance with a first embodiment of this invention. Emissivity probe 10 principally comprises tube assembly 12 which is attached to sensor housing assembly 14 by flange assembly 16. Bulkhead 18 is provided for mounting the device to an associated boiler inner wall 19 through a port 21(shown in FIG. 2) which enables tube assembly 12 to project into the interior 23 of the boiler, while sensor housing assembly 14 is external to the interior of the boiler and thus protected from the severe environment of the boiler interior. The steam tubes 25 are shown as part of inner wall 19. To facilitate installation, port 21 is preferably lined with port tube 26, which is attached at one end to outer wall 27 and at the other end to inner wall 19.

Figure 2:
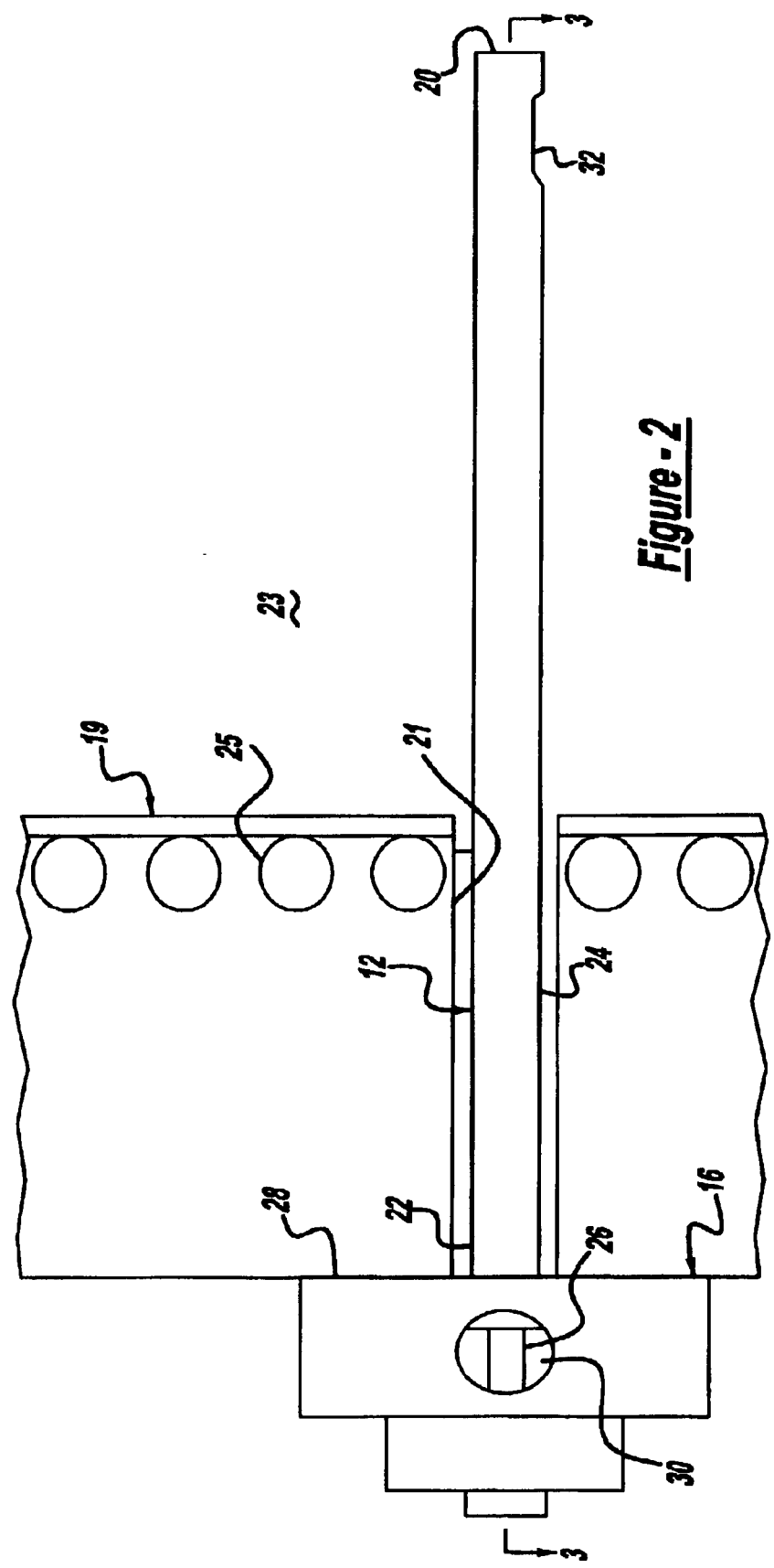
FIG. 2 is a side elevational view of the emissivity probe shown in FIG. 1 with the sensor housing assembly removed.

FIG. 2 shows tube assembly 12 apart from sensor housing assembly 14. Tube assembly 12 defines distal end 20 and proximal end 22 which is supported by flange assembly 16. Further references in this description to "proximal end" are used to describe components or features at or near flange assembly 16, whereas references to "distal end" are used to describe components or features at or near the free end (20) of the tube assembly 12.

Figure 3:
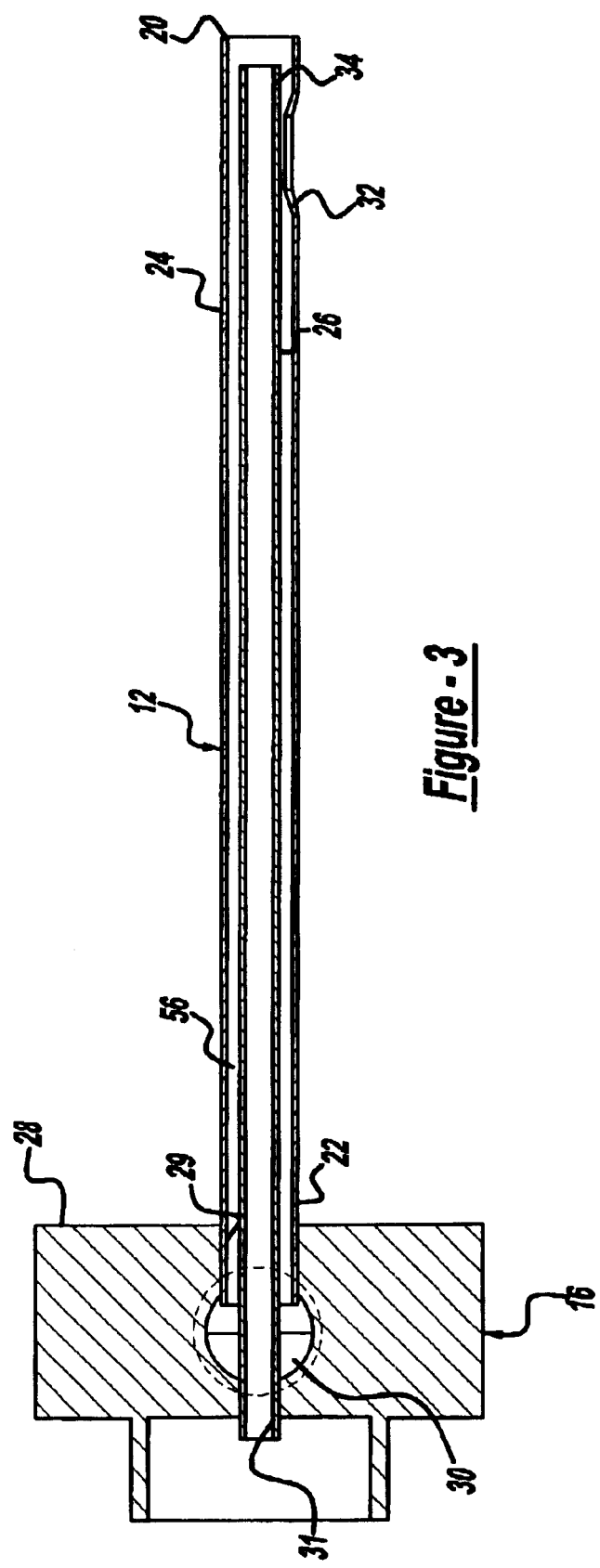
FIG. 3 is a cross-sectional view through the emissivity probe component shown in FIG. 2 taken along line 3—3 from FIG. 2.

FIG. 3 shows in cross-section internal components of tube assembly 12 and flange assembly 16. As shown, tube assembly 12 includes outer tube 24 and inner tube 26. Outer tube 24 is a hollow cylinder and open at both its proximal and distal ends. Outer tube 24 is mounted to flange 28 through bore 29, such that its proximal end communicates with cooling fluid supply passageway 30. Outer tube 24 further includes an aperture or window 32 positioned adjacent to the tube's distal end. Outer tube 24 is permanently fastened to flange 28 by welding, brazing, through interference fit, or using other attachment approaches.

Inner tube 26 is disposed within outer tube 24 in a co-axial manner and is also a hollow cylinder open at both its proximal and distal ends. However, the proximal end of inner tube 26 passes through cooling fluid supply passageway 30 and through bore 31. The distal end of inner tube 26 is recessed slightly from the distal end of outer tube 24 as shown in FIG. 3. Inner tube 26 features a cut-out 34 at its distal end. Windows 32 and cut-out 34 cooperate to provide clearance for optical guides which are contained within inner tube 26, as will be described in further detail later in this description. For durability and resistance to corrosion considerations, outer and inner tubes 24 and 26 are preferably made of stainless steel. For ease of installation, outer tube 24 preferably has a small outside diameter (for example, three-quarters of an inch or less).

Figure 4:
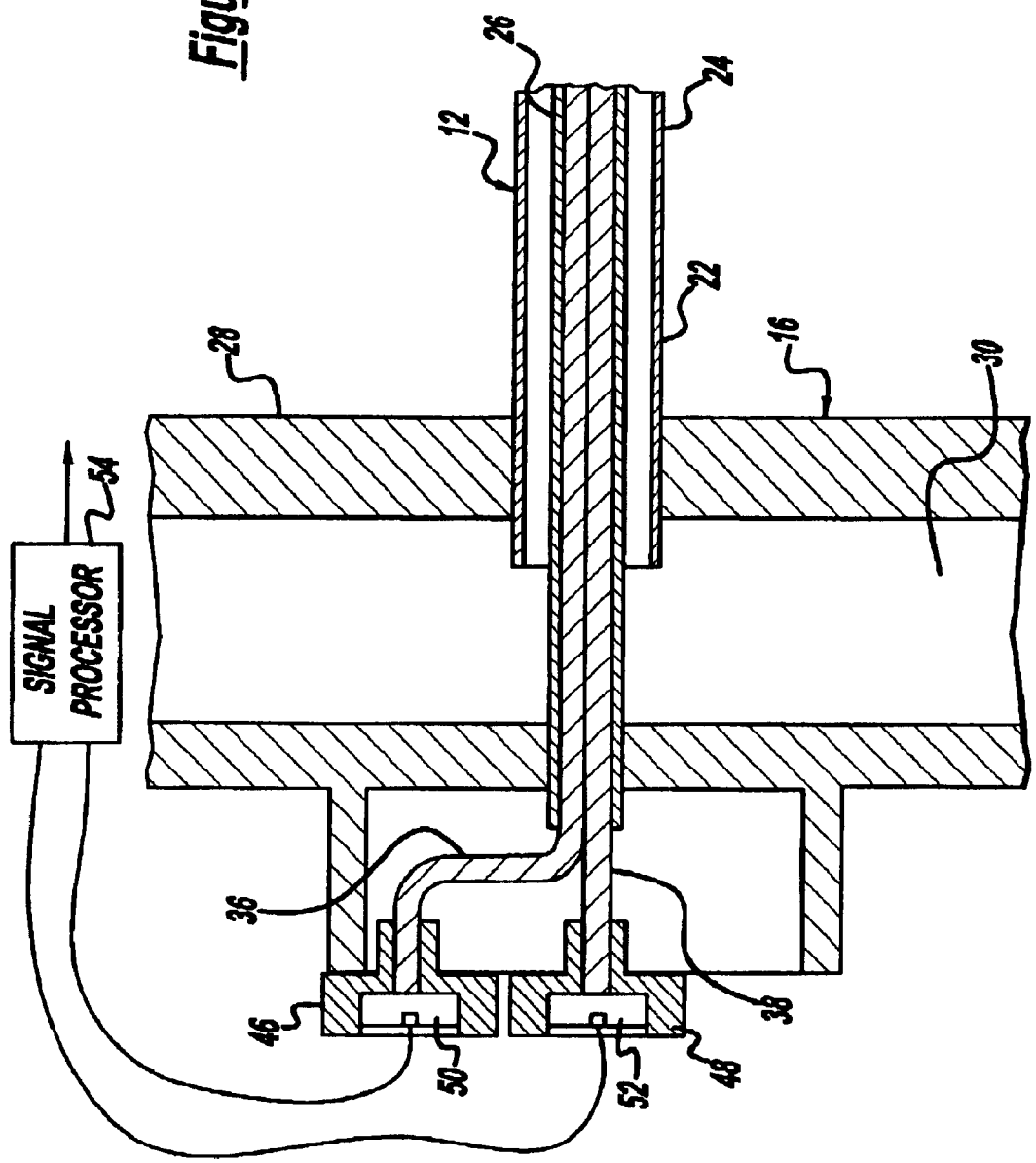
FIG. 4 is a cross-sectional view taken through the proximal end of the tube assembly.

FIG. 4 shows the details of the proximal end of emissivity probe 10 when it is fully assembled with incident optical guide 36 and reflective optical guide 38 installed in position within inner tube 26. Additional details of the incident and reflective optical guides 36 and 38 are provided with reference to FIGS. 6 and 7. Incident guide 36 features a pair of bends 40 and 42 such that its proximal end is parallel but displaced from the main axis of the guide. The distal end of incident guide 36 is straight and receives light inputs from light rays within an incident "cone" and along its longitudinal axis or "field of view" (FOV) as will be described in further detail in the following description. Reflective guide 38 is generally straight but has a hooked distal end 44. Incident guide 36 can be inserted into inner tube 26 from the proximal end of the inner tube whereas reflective guide 38 can be inserted into the opposite distal end of the inner tube.

Various optical guide types may be used for forming incident and reflective optical guides 36 and 38. However, the optical guide system chosen must possess the features of high resistance to heat, not have excessive bend sensitivity, and must be durable in the severe operating environment of a boiler interior.

These inventors have found that so-called "image conduits" are an ideal guide type for incident and reflective optical guides 36 and 38. Image conduits are rods made of many individual optical fibers. The fibers are bundled and fused together with ground polished faces at their distal and proximal ends. Each guide made of an image conduit 36 and 38 is a bundle of several thousand individual fibers which are normally used to provide the ability to project and transmit images, with each fiber providing an individual "pixel". In this application, however, imaging is not accomplished or intended. However, the ability for the image conduits of this type to be bent to the orientations shown in FIGS. 6 and 7, and their heat resistance, flexibility and durability make them ideally suited for the present application. In an application of this invention, guides 36 and 38 were comprised of image conduits each having bundles of fibers of a 25 micron diameter with three thousand individual optical fibers. These image conduits have a maximum operating temperature up to 850° F. and have a melting temperature of 1,200° F. The polished ends of the image conduits comprising optical guides 36 and 38 provide a field of view angle of about 64°, as shown in FIGS. 6 and 7.

FIG. 4 illustrates that when incident and reflective guides 36 and 38 are disposed within inner tube 26, their proximal ends terminate in a pair of photodiode adapters 46 and 48. Sensor elements shown as photodiodes 50 and 52 are disposed within adapters 46 and 48 and receive light signal transmissions through guides 36 and 38.

Optical filters 51 and 53 are positioned between the ends of optical guides 36 and 38 and their respective photodiodes 50 and 52 so that probe 10 is sensitive to a limited spectral band of light. For coal burning boilers, an ideal maximum fireball temperature is about 3,300° F. which, according to well known principles of black body radiation, produces an intensely peak light output (or center wavelength) at a wavelength of 1.39 microns (micro-meters). More common temperatures are about 3,000° F., which correspond to a center wavelength of about 1.5 microns. By selecting filters 51 and 53 to have a band pass characteristic, with their maximum transmissivity occurring at around a wavelength of 1.4 to 1.5 microns, a high signal level will be available for measurement. The filters 51 and 53 should have a band pass range (defined as the difference in wavelength bounded by where a reduction of transmissivity of 50% of the maximum occurs) of around 200 nanometers. It should be noted that the characteristics of optical guides 36 and 38, and photodiodes 50 and 52 could be selected such that the combination is inherently sensitive over the previously described wavelength range without the use of filters 51 and 53.

Although, as described above, designing probe 10 to be sensitive of over a limited range corresponding to the maximum intensity of the fireball produces the highest output for measurement, it is also possible to operate over a broader wavelength range. Such a range is believed to be bounded by wavelengths of between 0.4 and 4.0 m micrometers.

Figure 5:
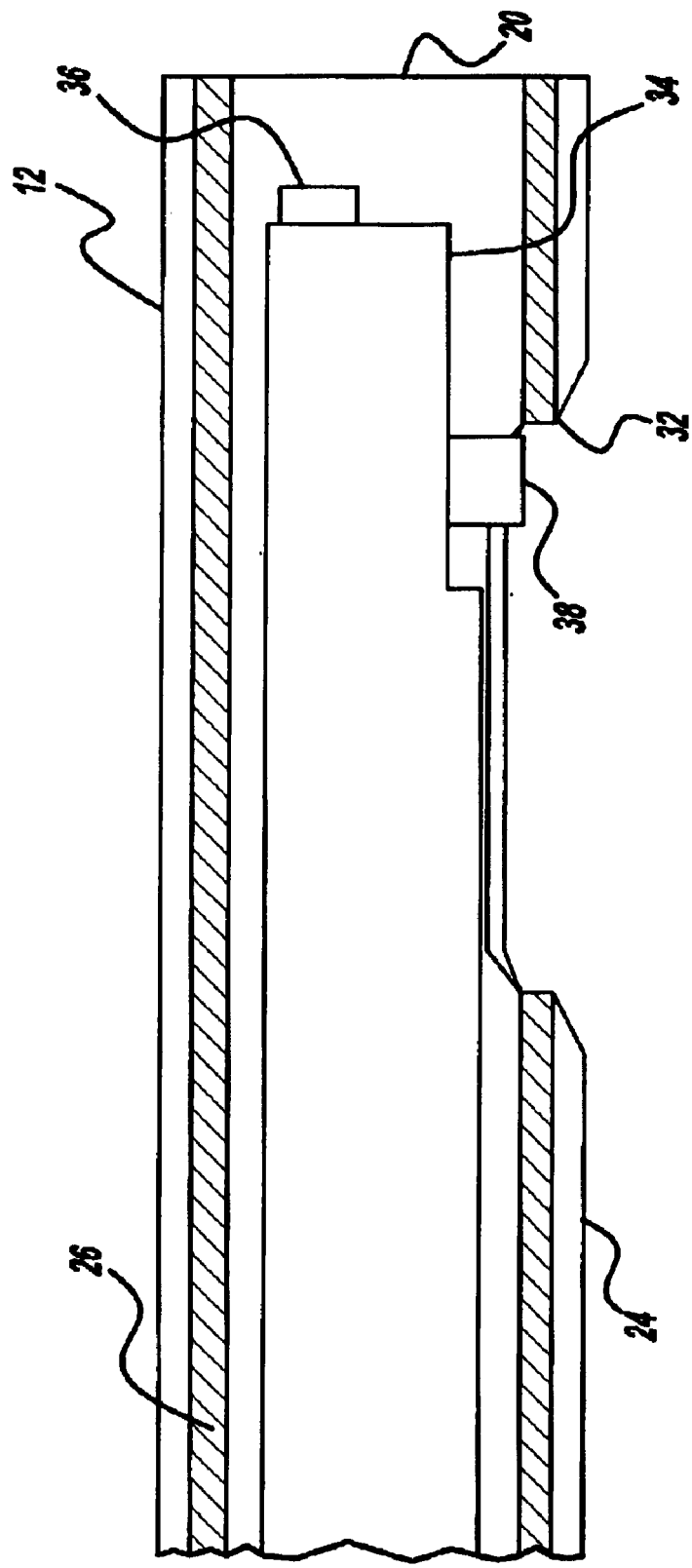
FIG. 5 is a cross-sectional view through the distal end of the tube assembly of the emissivity probe.
Figure 8:
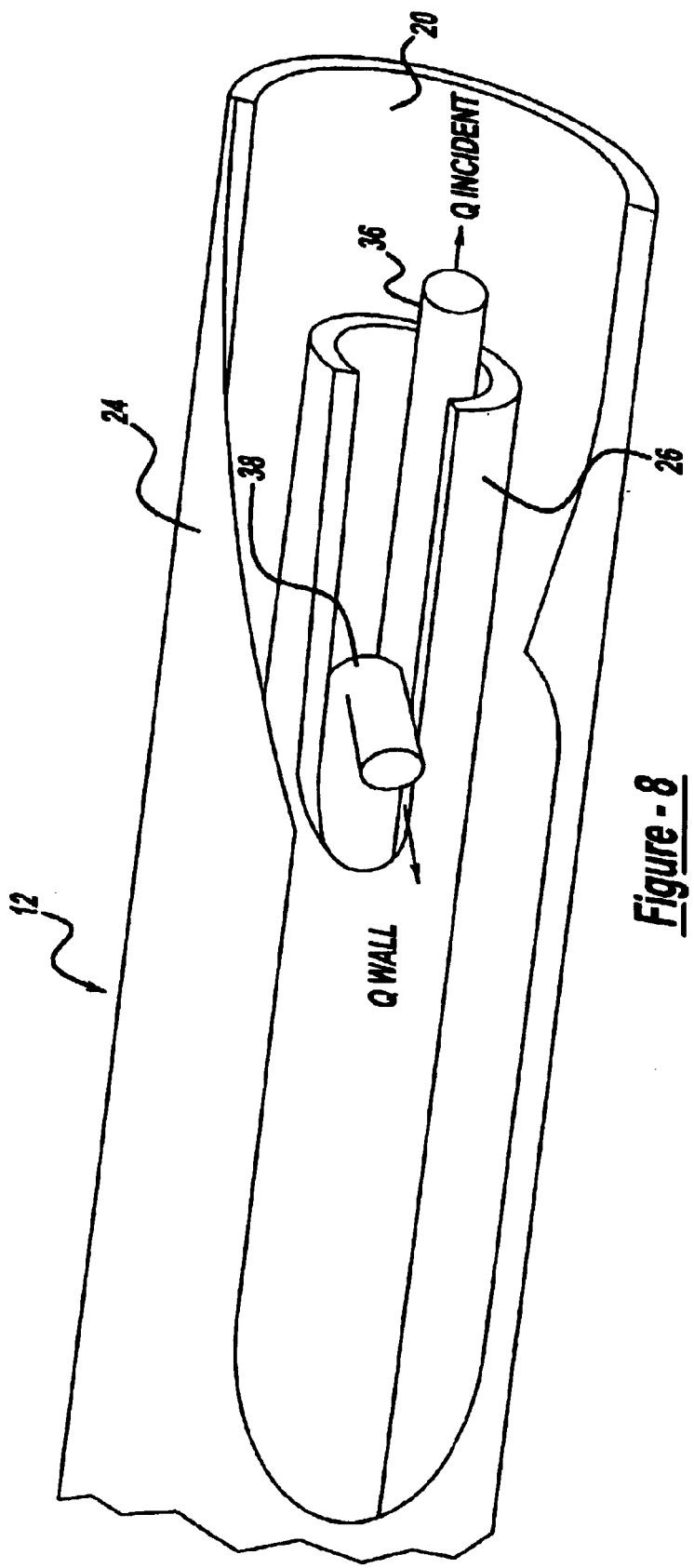
FIG. 8 is a pictorial view of the distal end of the tube assembly of the emissivity probe as shown in FIG. 1.

Now with particular reference to FIGS. 5 and 8, the distal end of tube assembly 12 is described in more detail. As illustrated, the distal end of incident guide 36 protrudes slightly from inner tube 26 and is oriented in a forward looking direction. In other words, the incident cone defining the field of view (FOV) of guide 36 is oriented concentrically with the longitudinal axis of tube assembly 12. The distal end of incident guide 36 is also recessed slightly from the distal end of outer tube 24. This orientation is provided to reduce the fouling of the sensitive distal end of incident guide 36. Reflective guide hooked end 44 extends through inner tube cut-out 34. Outer tube window 32 is provided to give the distal end of reflective guide 38 a "view" of the boiler wall surface. The distal end is also recessed within the cylinder defined by outer tube 24 for fouling protection. In other words, the cone defining the field of view of reflective guide 38 is not obstructed by outer tube 24, due to the provision of window 32. Thus light along a direction from the boiler wall is received by reflective guide 38. The direction of the field of view of reflective guide 38 is at a reverse angle from the direction of incident guide 36, i.e. they form an angle of greater than 90°.

As best shown in FIG. 4, light rays entering the distal ends of incident and reflective guides 36 and 38 are transmitted along the guides and are emitted at their proximal ends onto the associated photodiodes 50 and 52. The electrical outputs of the photodiodes are processed by signal processor 54 such that their relative values are compared. A ratio or difference calculation allows the reflected signal transmitted through reflective guide 38 to be compared with the "source" radiation emanating from the fireball of the boiler interior, transmitted through incident guide 36. Due to time dependent changes within the boiler interior 23, such as flame flicker, smoke, and turbulence, it is necessary to detect both the incident and reflective radiation signals in order to measure reflectance and therefore emissivity. Preferably, the signals from photodiodes 50 and 52 are also processed by processor 54 to provide some time averaging to remove high frequency effects, such as flame flicker. The signal processing requirements of processor 54 are not complex, since the outputs from photodiodes 50 and 52 are single channel outputs, each indicating a single intensity level which varies over time.

While tube assembly 12 is inserted within the boiler, air flow through passageway 30 enters the annular cooling fluid passageway 56 between inner and outer tubes 24 and 26. In addition to cooling the guides 36 and 38, this flow of flushing air (or other fluid) reduces the likelihood that contaminants will directly contact the distal ends of guides 36 and 38.

Figure 9:
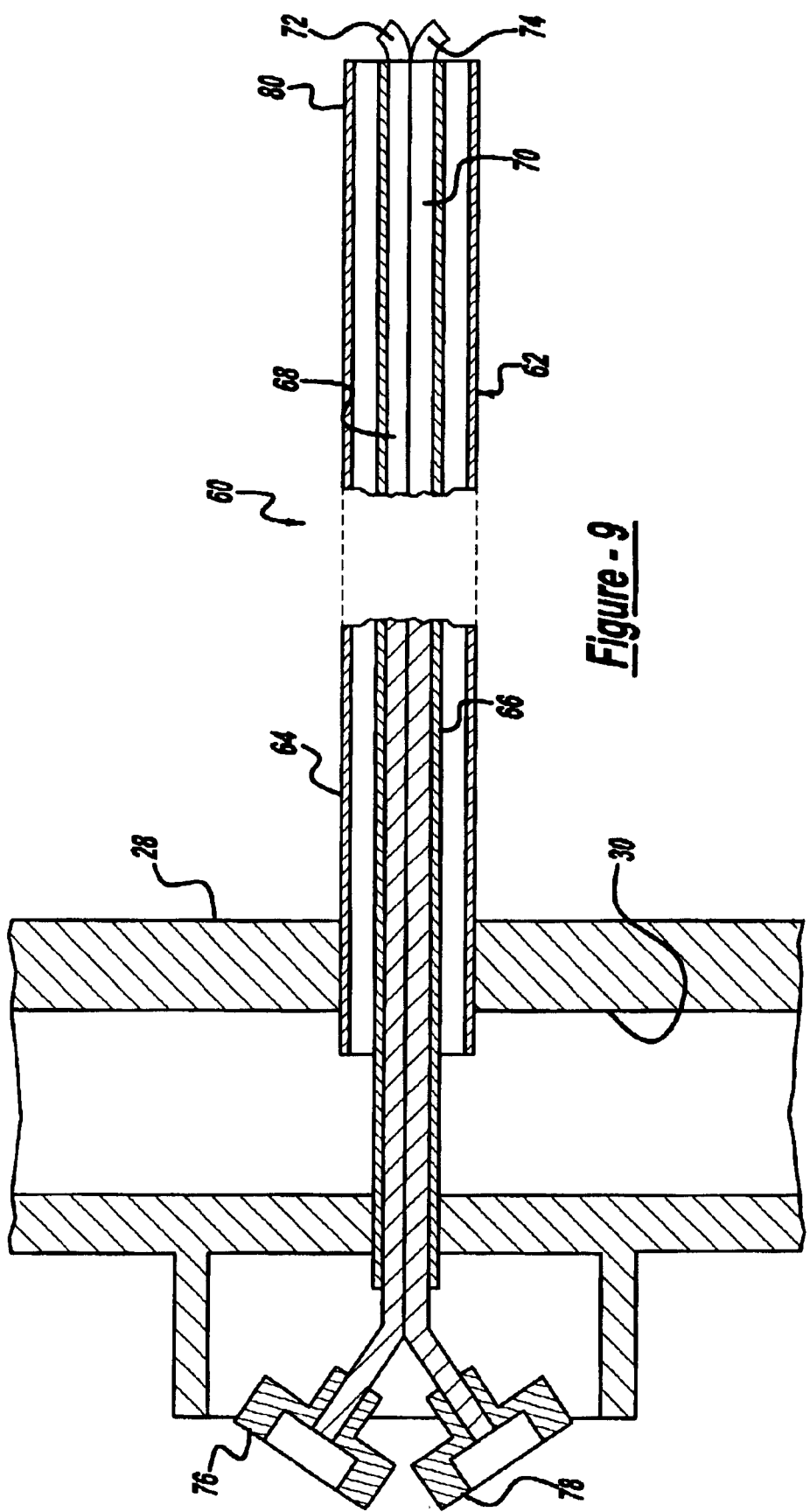
FIG. 9 is a cross-sectional view through an emissivity probe in accordance with a second embodiment of this invention.

Now with reference to FIG. 9, a second embodiment of an emissivity probe in accordance with this invention is shown which is generally designated by reference number 60. Emissivity probe 60 features a tube assembly 62 which differs from that previously described. In this instance, outer tube 64 and inner tube 66 do not feature the windows for "side looking" by a reflected optical guide. Rather, each of the guides 68 and 70 have bent ends 72 and 74 for receiving radiation in different directions. Emissivity probe 60 could be used in installations where one of the guide ends 72 or 74 can be directed to an adjacent wall surface, whereas the other guide end is oriented toward the boiler fireball.

Emissivity probe 60 also differs from probe 10 in that the proximal ends of guides 68 and 70 are bent to diverge. Photodiode adapters 76 and 78 are provided for the same function as previously described. Filters such as filters 51 and 53 shown in FIG. 4 may also be provided. For this embodiment of emissivity probe 60, cooling air flow is also provided to cool guides 68 and 70 and reduce the accumulation of deposits on their distal bent ends 72 and 74. The distal ends of guides 68 and 70 are approximately flush with the distal end of outer tube 64. At that distal end, outer tube 64 has a reduced diameter end 80 which increases the velocity of the cooling air flow, aiding in preventing contamination of the distal ends of guides 68 and 70.

Emissivity probe 60 preferably uses guides 68 and 70 of the type previously described; namely, so-called image conduits comprised of a large number of small diameter individual optical fibers which are bonded together. The advantageous attributes of such products previously described and are equally attractive for implementation with emissivity probe 60.

While the above description constitutes the preferred embodiment of the present invention, it will be appreciated that the invention is susceptible to modification, variation and change without departing from the proper scope and fair meaning of the accompanying claims.

We claim:

1. An emissivity probe for measuring the reflectivity of a surface of a boiler for use in controlling boiler cleaning systems and of a type adapted to be mounted to an exterior wall of the boiler, comprising;
   a flange assembly adapted to be mounted to the boiler wall;
   a tube assembly defining a proximal end affixed to the flange assembly and a distal end for extending into the boiler interior, the tube assembly having an outer tube and an inner tube extending coaxially within the outer tube, the inner and outer tubes cooperating to define an annular cooling fluid passageway, at least two optical guides located within the inner tube extending between distal and proximal ends of the inner tube, ends of the first and second optical guides positioned adjacent to the distal end of the inner tube and oriented to receive light inputs from two different first and second directions respectively from within the boiler interior, wherein the first direction is oriented to receive light directly from the combustion process within the boiler interior and the second direction is oriented to receive light reflected by the surface of the boiler;
   a cooling fluid supply for causing a flow of cooling fluid through the annular coolant fluid passageway; and
   a first and a second sensor located adjacent the proximal end of the first and second optical guides respectively adapted to receive light signals transmitted by the optical guides, the emissivity being associated with the ratio of the reflected light intensity from the surface of the boiler to the light intensity from the combustion process.

2. An emissivity probe according to claim 1 wherein light directed to the first and second sensors is in a wavelength range of 0.4 to 4.0 microns.

3. An emissivity probe according to claim 2 wherein the light directed to the first and second sensors has a maximum intensity at about 1.4 to 1.5 microns.

4. An emissivity probe according to claim 1 wherein the first direction is concentric with the tube assembly and projects forward from the distal end of the tube assembly and the second direction is at a reverse angle.

5. An emissivity probe according to claim 1 wherein the first optical guide has a straight distal end and is oriented to extend from an open distal end of the inner tube and the second optical guide has a hooked distal end and the inner tube includes a cut-out with the second optical guide hooked end extending through the cut-out.

6. An emissivity probe according to claim 5 wherein the outer tube includes a window oriented in a field of view of the second optical guide.

7. An emissivity probe according to claim 1 wherein the first and second optical guides are image conduits each having a plurality of individual optical fibers which are fused together.

8. An emissivity probe according to claim 1 wherein the first and second optical guides have a field of view of about 64 degrees.

9. An emissivity probe according to claim 1 wherein the first and second optical guides each have a bent distal end.

10. An emissivity probe according to claim 1 wherein the outer tube has a reduced diameter at the outer tube distal end to increase the velocity of the cooling fluid.

11. An emissivity probe according to claim 1 further comprising a signal processor for receiving signals from the first and second sensors and measuring the intensity of light incident on the first and second sensors and further for comparing the intensity values associated with each of the first and second sensors to thereby obtain a measure of the reflectivity of the surface of the boiler.

12. An emissivity probe according to claim 1 further comprising first and second filters positioned between first and second sensors and the respective optical guides, the filters having a band pass characteristic.

13. An emissivity probe according to claim 12 wherein the filters have a maximum transmissivity at a wavelength of about 1.4 to 1.5 micrometers.

14. An emissivity probe for measuring the reflectivity of a surface of a boiler for use in controlling boiler cleaning systems and of a type adapted to be mounted to an exterior wall of the boiler, comprising;
   a flange assembly adapted to be mounted to the boiler wall;
   a tube assembly defining a proximal end affixed to the flange assembly and a distal end for extending into the boiler interior, the tube assembly having an outer tube and an inner tube extending coaxially within the outer tube, the inner and outer tubes cooperating to define an annular cooling fluid passageway, at least two optical guides located within the inner tube extending between distal and proximal ends of the inner tube, the optical guides each having a plurality of individual optical fibers, ends of the first and second optical guides positioned adjacent to the distal end of the inner tube and oriented to receive light inputs from two different first and second directions respectively from within the boiler, wherein the first direction is coaxial with the longitudinal axis of the tube assembly and oriented to receive light directly from the combustion process within the boiler and the second direction at an angle from the longitudinal axis of the tube assembly and is oriented to receive light reflected by the surface of the boiler;

a cooling fluid supply for causing a flow of cooling fluid through the annular coolant fluid passageway; and a first and a second sensor located adjacent the proximal end of the first and second optical guides respectively adapted to receive light signals transmitted by the optical guides, the emissivity being associated with the ratio of the reflected light intensity from the surface of the boiler to the light intensity from the combustion process.

15. An emissivity probe according to claim 14 wherein light directed to the first and second sensors is in a wavelength range of 0.4 to 4.0 microns.

16. An emissivity probe according to claim 15 wherein the filters have a maximum transmissivity at a wavelength of about 1.4 to 1.5 micrometers.

17. An emissivity probe according to claim 14 wherein the first optical guide has a straight distal end and is oriented to extend from an open distal end of the inner tube and the second optical guide has a hooked distal end and the inner tube includes a first cut-out with the second optical guide hooked end extending through the cut-out.

18. An emissivity probe according to claim 17 wherein the outer tube includes a window oriented in a field of view of the second optical guide.

19. An emissivity probe according to claim 14 wherein the first and second optical guides have a field of view of about 64 degrees.

20. An emissivity probe according to claim 14 wherein the outer tube has a reduced diameter at the outer tube distal end to increase the velocity of the cooling fluid.

21. An emissivity probe according to claim 14 further comprising a signal processor for receiving signals from the first and second sensors and measuring the intensity of light incident on the first and second sensors and further for comparing the intensity values associated with each of the first and second sensors to thereby obtain a measure of the reflectivity of the surface of the boiler.

22. An emissivity probe according to claim 14 further comprising first and second filters positioned between first and second sensors and the respective optical guides, the filters having a band pass characteristic.

23. An emissivity probe according to claim 22 wherein the filters have a maximum transmissivity at a wavelength of about 1.4 to 1.5 micrometers.

24. An emissivity probe for measuring the reflectivity of a surface of a boiler for use in controlling boiler cleaning systems and of a type adapted to be mounted to an exterior wall of the boiler, comprising:

a flange assembly adapted to be mounted to the boiler wall;

a tube assembly defining a proximal end affixed to the flange assembly and a distal end for extending into the boiler interior, the tube assembly having an outer tube and an inner tube extending coaxially within the outer tube, the inner and outer tubes cooperating to define an annular cooling fluid passageway, at least two optical guides located within the inner tube extending between distal and proximal ends of the inner tube the optical guides each having a plurality of individual optical fibers, ends of the first and second optical guides positioned adjacent to the distal end of the inner tube and oriented to receive light inputs from two different first and second directions respectively from within the boiler, wherein the first direction is oriented to receive light directly from the combustion process within the boiler interior and the second direction is oriented to receive light reflected by the surface of the boiler and wherein the first and the second directions are angled from the longitudinal axis of the tube assembly;

a cooling fluid supply for causing a flow of cooling fluid through the annular coolant fluid passageway; and a first and a second sensor located adjacent the proximal end of the first and second optical guides respectively adapted to receive light signals transmitted by the optical guides, the emissivity being associated with the ratio of the reflected light intensity from the surface of the boiler to the light intensity from the combustion process.

25. An emissivity probe according to claim 24 wherein light directed to the first and second sensors is in a wavelength range of 0.4 to 4.0 microns.

26. An emissivity probe according to claim 25 wherein the light directed to the first and second sensors has a maximum intensity at about 1.4 to 1.5 microns.

27. An emissivity probe according to claim 24 wherein the first and second optical guides have a field of view of about 64 degrees.

28. An emissivity probe according to claim 24 wherein the first and second optical guides each have a bent distal end.

29. An emissivity probe according to claim 24 wherein the outer tube has a reduced diameter at the outer tube distal end to increase the velocity of the cooling fluid.

30. An emissivity probe according to claim 24 further comprising a signal processor for receiving signals from the first and second sensors and measuring the intensity of light incident on the first and second sensors and further for comparing the intensity values associated with each of the first and second sensors to thereby obtain a measure of the reflectivity of the surface of the boiler.

31. An emissivity probe according to claim 30 further comprising first and second filters positioned between first and second sensor and the respective optical guides, the filters having a band pass characteristic.

32. An emissivity probe according to claim 31 wherein the filters have a maximum transmissivity at a wavelength of about 1.4 to 1.6 micrometers.

33. A monitoring system for measuring the reflectivity of a surface of a boiler for use in controlling boiler cleaning systems and of a type adapted to be mounted to an exterior wall of the boiler, comprising;

an emissivity probe having, a tube assembly defining a proximal end affixed to the wall of the boiler and a distal end for extending into the boiler interior, and having at least two optical guides located within the tube assembly extending between distal and proximal ends of the tube assembly, ends of the first and second optical guides positioned adjacent to the distal end of the tube assembly and oriented to receive light inputs from two different first and second directions respectively from within the boiler interior, wherein the first direction is oriented to receive light directly from the combustion process within the boiler interior and the second direction is oriented to receive light reflected by the surface of the boiler;

a first and a second sensors located adjacent the proximal and of the first and second optical guides respectively adapted to receive light signals transmitted by the optical guides, the sensors sensitive to light having a wavelength of 0.4 to 4.0 microns; and a signal processor for receiving signals from the first and second sensors and measuring the intensity of light incident on the first and second sensors and further for comparing the intensity values associated with each of the first and second sensors to thereby obtain a measure of the reflectivity of the surface of the boiler to determine an emissivity of the surface of the boiler, the emissivity being associated with the ratio of the reflected light intensity from the surface of the boiler to the light intensity from the combustion process.

34. An emissivity probe according to claim 33 wherein the first direction is concentric with the tube assembly and the second direction is at a reverse angle.

35. An emissivity probe according to claim 33 wherein the first and second optical guides are image conduits each having a plurality of individual optical fibers.

36. An emissivity probe according to claim 33 wherein the first and second optical guides have a field of view of about 64 degrees.

37. An emissivity probe according to claim 33 wherein the first and second optical guides each have a bent distal end.

38. An emissivity probe according to claim 33 further comprising first and second filters positioned between first and second sensors and the respective optical guides, the filters having a band pass characteristic.

39. An emissivity probe according to claim 38 wherein the filters have a maximum transmissivity at a wavelength of about 1.4 to 1.5 micrometers.

40. A method for measuring the reflectivity of a surface of a boiler for use in controlling boiler cleaning systems, comprising the steps of;

providing an emissivity probe defining a proximal end affixed to a wall of the boiler and a distal end for extending into the boiler interior the probe having at least two optical guides extending between distal and proximal ends of the probe, ends of the first and second optical guides positioned adjacent to the distal end of the probe and oriented to receive light inputs from two different first and second directions respectively from within the boiler interior, wherein the first direction is oriented to receive light directly from the combustion process within the boiler and the second direction is oriented to receive light reflected by the surface of the boiler;

providing a first and a second sensor located adjacent the proximal ends of the first and second optical guides respectively adapted to receive light signals transmitted by the optical guides wherein the first and second sensors are sensitive to light of a wavelength in a range of 0.4 to 4.0 microns;

providing a signal processor for receiving electrical signals from the first and second sensors which are rotated to the intensities of light incident on the first and second sensors; and the signal processor comparing the intensity values and generating a value related to the emissivity of the surface of the boiler, the emissivity being associated with the ratio of the reflected light intensity from the surface of the boiler to the light intensity from the combustion process.

41. The method according to claim 40 wherein the signal processor calculates a difference value related to the emissivity of the surface of the boiler.

42. The method according to claim 40 wherein the signal processor calculates a ratio value related to the emissivity of the surface of the boiler.

* * * * *